United States Patent
Kudavelly et al.

(10) Patent No.: US 8,867,027 B2
(45) Date of Patent: Oct. 21, 2014

(54) APPARATUS AND METHOD FOR ESTIMATING BILIRUBIN CONCENTRATION USING REFRACTOMETRY

(75) Inventors: Srinivas Rao Kudavelly, Bangalore (IN); Eduard Johannes Meijer, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 11 days.

(21) Appl. No.: 13/701,058

(22) PCT Filed: Apr. 27, 2011

(86) PCT No.: PCT/IB2011/051859
§ 371 (c)(1),
(2), (4) Date: Nov. 30, 2012

(87) PCT Pub. No.: WO2011/151743
PCT Pub. Date: Dec. 8, 2011

(65) Prior Publication Data
US 2013/0070230 A1    Mar. 21, 2013

Related U.S. Application Data

(60) Provisional application No. 61/351,092, filed on Jun. 3, 2010.

(51) Int. Cl.
*G01N 33/48*    (2006.01)
*G01N 21/41*    (2006.01)
*G01N 33/49*    (2006.01)

(52) U.S. Cl.
CPC ............ *G01N 21/4133* (2013.01); *G01N 33/49* (2013.01); *G01N 2021/414* (2013.01)
USPC .......................................................... 356/40

(58) Field of Classification Search
CPC ............................... G01N 33/48; G01N 21/41
USPC ....................................................... 356/40, 128
See application file for complete search history.

(56) References Cited

U.S. PATENT DOCUMENTS 3,267,795 A * 8/1966 Goldberg ...................... 356/137
(Continued)

FOREIGN PATENT DOCUMENTS

WO    2005001453 A1    1/2005

OTHER PUBLICATIONS

F. William Sunderman; "A Rapid Method for Estimating Serum Proteins Formula for Calculating Serum Protein Concentration From the Refractive Index of Serum", The Journal of Biological Chemistry, Apr. 1944, vol. 153, pp. 139-142.
Jess G. Thoene et al; "Use of the Hand Refractometer in Determining Total Serum Proteins of Infants and Children", The Journal of Pediatrics, Sep. 1967, vol. 71, No. 3, pp. 413-417.

(Continued)

*Primary Examiner* — Roy M Punnoose

(57) ABSTRACT

A bilirubin measuring apparatus includes a sample holding portion for holding at least a sample to be analyzed, a light source for directing light toward the sample holding portion, and means for determining a concentration of bilirubin in the sample based on an amount which the light is refracted while passing through the sample holding portion when at least the sample is held at the sample holding portion. Also, a method of measuring bilirubin in a sample includes holding at least the sample at a sample holding position, directing light toward the sample holding position so that the light will pass through the sample, and determining a concentration of bilirubin in the sample based on an amount which the light is refracted while passing through the sample holding position.

17 Claims, 4 Drawing Sheets

(56) References Cited

U.S. PATENT DOCUMENTS

| | | | |
|---|---|---|---|
| 3,625,620 A * | 12/1971 | Goldberg | 356/135 |
| 4,267,844 A | 5/1981 | Yamanishi | |
| 4,650,323 A | 3/1987 | Nakagawa | |
| 5,305,071 A | 4/1994 | Wyatt | |
| 5,355,211 A * | 10/1994 | Thompson et al. | 356/135 |
| 5,772,606 A * | 6/1998 | Ashibe et al. | 600/573 |
| 5,969,808 A * | 10/1999 | Cotton et al. | 356/135 |
| 6,045,502 A * | 4/2000 | Eppstein et al. | 600/306 |
| 6,195,160 B1 * | 2/2001 | Rainer et al. | 356/135 |
| 6,365,109 B1 * | 4/2002 | Jeng et al. | 422/547 |
| 6,396,576 B1 | 5/2002 | Bleyle | |
| 6,426,045 B1 * | 7/2002 | Jeng et al. | 422/82.05 |
| 7,369,221 B2 * | 5/2008 | Amamiya et al. | 356/135 |
| 2002/0159050 A1 | 10/2002 | Sharma et al. | |

OTHER PUBLICATIONS

W.H. Marsh et al; "Serum Protein Determination by Automatic Recording Refractometry", Clin. Chem. Laboratory, Kings CT Hospital, Brooklyn, NY, Dec. 1962, vol. 8, BI, 6M pp. 640-646.

John M. Steinke et al; "Rapid Spectrophotometric Measurements of Total Bilirubin in Intact and Hemolyzed Neonatal Blood: A Feasibility Study", Journal of Perinatology, 2001, vol. 21, pp. 382-387.

"Management of Hyperbilirubinemia in Teh Newborn Infant 35 or More Weeks of Gestation", Pediatrics Official Journal of the American Academy of Pediatrics, vol. 114, No. 1, Jul. 2004, pp. 297-316.

Derek Watson et al; "A Study of Six Representative Methods of Plasma Bilirubin Ananlysis", Journal Clin. Path., 1961, vol. 14, pp. 271-278.

* cited by examiner

| S.No | Concentration of Bilirubin (mg / dL) | Angle of Refraction (deg) |
|---|---|---|
| 1 | 5 | 20 |
| 2 | 10 | 25 |
| 3 | 15 | 27 |
| 4 | 20 | 30 |
| 5 | 25 | 32 |

APPARATUS AND METHOD FOR ESTIMATING BILIRUBIN CONCENTRATION USING REFRACTOMETRY

The present invention relates to the estimation of bilirubin levels in individuals, such as neonates, and more specifically, to an apparatus and method of Neonatal jaundice is a yellowing of the skin and other tissues of a newborn infant. Neonatal jaundice affects approximately 60% of full-term and approximately 80% of pre-term infants globally. Management of jaundiced neonates typically requires the measurement and monitoring of total serum bilirubin (TSB), which is most commonly determined by analyzing a plasma or serum sample from the infant (typically, a bilirubin level of more than 5 mg/dL manifests clinical jaundice in neonates).

Thus, the measurement of total serum bilirubin (TSB) is one of the most frequently performed tests in newborns. In fact, management guidelines established by the American Academy of Pediatrics are based on specific quantitative measurements of total bilirubin in blood. In addition, the appropriate management of patients with neonatal hyperbilirubinemia usually requires repeated measurements of TSB to detect trends such as rising or falling bilirubin levels. However, hospital turnaround time between obtaining a blood sample and receiving results from a central clinical laboratory often slows the pediatrician's management of healthy and hyperbilirubinemic neonates and results in delaying the discharge of mother and child from the hospital, thereby increasing healthcare costs. In addition, the most frequent cause of hospital readmissions for neonates is due to rebound jaundice caused by inefficient assessment of hyperbilirubinemia.

Based on the above, it is clear that methods for monitoring hyperbilirubinemia in a newborn that provide fast but reliable results from very small volumes of blood (thereby enabling bilirubin measurements at the point of care) are desirable. There is thus a significant clinical need for a portable instrument to make rapid, accurate (similar to laboratory method of evaluation), and convenient near-patient measurement of total serum bilirubin in neonates from very small volumes of blood.

In one embodiment, a bilirubin measuring apparatus is provided that includes a sample holding portion for holding at least a sample to be analyzed, a light source for directing light toward the sample holding portion, and means for determining a concentration of bilirubin in the sample based on an amount which the light is refracted while passing through the sample holding portion when at least the sample is held at the sample holding portion.

In another embodiment, a method of measuring bilirubin in a sample is provided that includes holding at least the sample at a sample holding position, directing light toward the sample holding position so that the light will pass through the sample, and determining a concentration of bilirubin in the sample based on an amount which the light is refracted while passing through the sample holding position.

In still another embodiment, a method of making a bilirubin measuring apparatus is provided that includes a sample holding portion for holding at least a sample to be analyzed, a light source for directing light toward the sample holding portion, and means for determining a concentration of bilirubin in the sample based on an amount which the light is refracted while passing through the sample holding portion when at least the sample is held at the sample holding portion, wherein the method includes using a plurality calibration samples each having a known concentration of bilirubin to determine an equation relating refractive index of bilirubin to bilirubin concentration, and using the equation to make the means for determining the concentration of bilirubin in the sample.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

Figure 1:
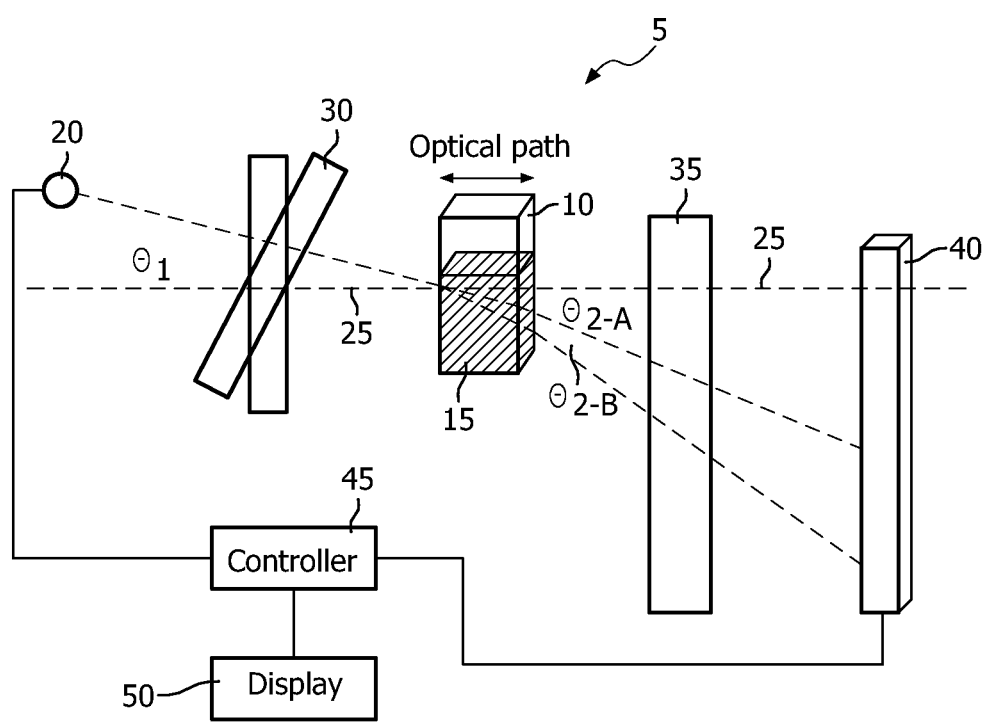
FIG. 1 is a schematic diagram of an exemplary apparatus that may be used to perform certain calibration measurements for use in making a device for estimating bilirubin concentration based on refractometry according to an embodiment of the invention.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As employed, herein, the statement that two or more parts or components are "coupled" together shall mean that the parts are joined or operate together either directly or through one or more intermediate parts or components.

As employed herein, the statement that two or more parts or components "engage" one another shall mean that the parts exert a force against one another either directly or through one or more intermediate parts or components.

As employed herein, the term "number" shall mean one or an integer greater than one (i.e., a plurality).

FIG. 1 is a schematic diagram of apparatus 5 according to an aspect of an exemplary embodiment of the present invention. As described in greater detail herein, apparatus 5 may be used to perform certain calibration measurements which then may be used in making a device for estimating bilirubin concentration using refractometry (various embodiments of which are described). Apparatus 5 includes sample holder 10, such as, without limitation, a non-disposable cuvette, a disposable cuvette, or a disposable micro-fluidic cartridge, structured to hold a liquid sample 15 therein. In the exemplary embodiment, the index of refraction of sample holder 10 is known, and is advantageously used to select the size, cost, and/or sensitivity of photodiode array 40 described below. As described in greater detail below, during the calibration phase employed in the exemplary embodiment of the present invention, liquid sample 15 is various blood serum samples having known bilirubin concentrations.

Apparatus 5 further includes light source 20 which is structured to emit light toward sample holder 10. As seen in FIG.

1, light source 20 is positioned so that it will emit light at a known angle $\theta_1$ with respect to normal 25 to the front surface of sample holder 10. Light source 20 may be a single light emitting device or a plurality of light emitting devices. For example, and without limitation, light source 20 may be an LED (or LEDs) which emits/emit white light or light of one or more particular wavelengths, or an incandescent light source (or sources) that emits/emit white light or light of one or more particular wavelengths. Apparatus 5 also includes lens system 30 which is structured to collimate the light emitted by light source 20 and direct it toward sample holder 10 (at an angle of incidence of $\theta_1$).

As seen in FIG. 1, light which is incident on sample holder 10 at angle $\theta_1$ will be refracted by sample holder 10 and liquid sample 15 and will exit sample holder 10 at an angle $\theta_2$ with respect to normal 15. The amount of refraction, and therefore the size of angle $\theta_2$, will vary depending on the concentration of bilirubin in liquid sample 15 (two such exemplary angles $\theta_2$ (labeled $\theta_{2\text{-}A}$ and $\theta_{2\text{-}B}$) are shown in FIG. 1, representing refraction caused by two different liquid samples 15 having two different bilirubin concentration levels). Apparatus 5 further includes filter 35 and photodiode array 40. In the exemplary embodiment, filter 35 is an optical narrow band filter that passes only wavelengths of interest to photodiode array 40. For example, for estimating bilirubin, the filter used in the exemplary embodiment is a 455 nm optical filter, which only allows the propagation of 455 nm wavelength light towards photodiode array 40. The rationale for using the 455 nm filter is that bilirubin has peak absorbance at that wavelength. Photodiode array 40 is an array of a number of linearly positioned photodiodes. As is known, a photodiode converts light into a current or voltage. By identifying the particular photodiode in photodiode array 40 that registers the peak intensity, the angle $\theta_2$ for the current liquid sample 15 can be determined. More specifically, since the position of photodiode array 40 with respect to sample holder 10 is known, the angle relative to normal 25 ($\theta_2$) for each photodiode in photodiode array 40 can be pre-computed and stored. While photodiode array 40 in the exemplary embodiment uses photodiodes, other types of photodetectors that convert light into a current or voltage may also be used to form a photodetector array that may be used instead of photodiode array 40.

In addition, as seen in FIG. 1, in the exemplary embodiment, apparatus 5 includes controller 45 that is operatively coupled to light source 20 for controlling light source 20 and to photodiode array 40 for reading photodiode array 40. Controller 45 includes a processing portion which may be, for example, a microprocessor, a microcontroller or some other suitable processing device, and a memory portion that may internal to the processing portion or operatively coupled to the processing portion and that provides a storage medium for data and software executable by the processing portion for controlling the operation of apparatus 5. In particular, controller may be programmed to turn light source 20 on and off, receive signals from photodiode array 40, determine the particular photodiode in photodiode array 40 that registers the peak intensity, and determine the angle $\theta_2$ that is associated with the particular photodiode in photodiode array 40 that registers the peak intensity. In addition, controller 45 is in the illustrated embodiment coupled to display 50, such as an LCD, for outputting determined angle $\theta_2$ for use as described herein, and, optionally, the intensity measured by each photodiode.

Figures 2, 3:
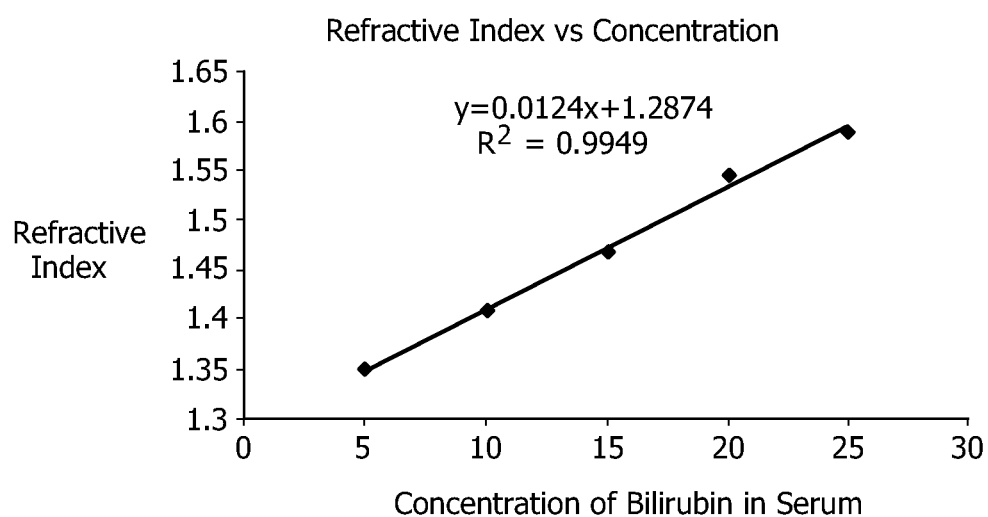
FIG. 2 is a table showing an example data set obtained using the apparatus of FIG. 1.
FIG. 3 is a graph showing the regression line for the example data shown in FIG. 2.

An exemplary embodiment of the calibration methodology of an aspect of the present invention will now be described. In the first calibration step, a reference serum is provided as liquid sample 15, wherein the reference serum is blood serum having a minimal amount (including none) of bilirubin therein (e.g., <2.5 mg/DL). Light source 20 is then caused to emit light and $\theta_2$ of the refracted, transmitted light is determined as described above. In the exemplary embodiment, that $\theta_2$ is used as a "zero" reference angle for the other angle measurements described below. Next, a number of different serum samples each having a different known bilirubin concentration are provided as liquid sample 15, and the associated angle $\theta_2$ is determined for each. In addition, the angle relative to the "zero" just described is also determined for each based on the determined $\theta_2$ (each such angle shall be referred to herein as an adjusted $\theta_2$). In between each measurement, sample holder 10 in the exemplary embodiment is cleaned. Alternatively, each serum sample may use its own similar disposable single use sample holder 10. Thus, following these steps, a set of data including the bilirubin concentration and the associated adjusted $\theta_2$ for each sample will have been obtained. FIG. 2 is a table showing an example of such a data set obtained for five serum samples 1-5 (in the table, the angle of refraction is the adjusted $\theta_2$).

In an alternative embodiment, after the "zero" reference angle is determined as described above, the photodetector array 40 is moved so that that "zero" reference angle is aligned with normal 25. Thereafter, each angle measurement will directly be an adjusted $\theta_2$.

Next, using Snell's law ($n_1 \sin \theta_1 = n_2 \sin \theta_2$), the effective refractive index for each liquid sample 15 is obtained (as used herein, the term "effective refractive index" shall mean the refractive index of the liquid sample 15 (serum/solvent including bilirubin), since the refractive index of the sample holder is known and invariant and the finite thickness of the sample holder is also known and invariant), wherein $n_1$ is the refractive index of air, $\theta_1$ is as shown in FIG. 1, $\theta_2$ is the adjusted $\theta_2$ described above and $n_2$ is the effective refractive index. Using ordinary least square fitting, a regression equation is then derived which relates effective refractive index (the dependent variable) to bilirubin concentration (the independent variable) in the sample holder 10 (the regression equation allows one to predict effective refractive index from bilirubin concentration). FIG. 3 is a graph showing the regression line for the example data shown in FIG. 2. The slope of the regression line in turn gives the extinction constant of the bilirubin (in the regression example shown in FIG. 3 it is 0.0124). Multiplying the extinction constant and molar mass of bilirubin (584.66 gm) will provide the molar absorptivity coefficient ($\epsilon$) for the bilirubin. Once the proper molar absorptivity coefficient ($\epsilon$) is known, an equation that provides bilirubin concentration as a function of refractive index (R) of bilirubin is as follows: $C(\text{mg/dL}) = R/\epsilon l$, wherein $l$ is the optical path length of the sample holder and liquid sample 15 as shown in FIG. 1 and R is the refractive index determined from Snell's law and the angles $\theta_1$ and adjusted $\theta_2$.

According to one particular, exemplary embodiment, once calibration in this manner is completed, the calibration information may be used to custom design a bilirubin measuring apparatus that employs a custom, manual refractometer to indicate estimated bilirubin concentration levels of serum samples in sample holder 10. In particular, in one embodiment, a conventional manual handheld refractometer reticle/scale (which normally shows refractive index) can be modified to directly depict bilirubin concentration by converting each refractive index value (normally depicted on the reticle/scale) to the corresponding bilirubin concentration as determined by the equation $C(\text{mg/dL}) = R/\epsilon l$. Alternatively, each refractive index (normally depicted on the reticle/scale) can be converted to a concentration on the reticle by adding a conversion factor to the refractive index based on the regression equation. For example, if the refractive index is 0.5, it may be directly mapped to show a concentration of 5 mg/dL as per the regression equation. In the exemplary embodiment, such a bilirubin measuring apparatus would have a small form factor and would be able to make accurate estimates of bilirubin concentration levels using relatively small sample volumes (since refractive index does not vary based on sample volume).

Figure 4:
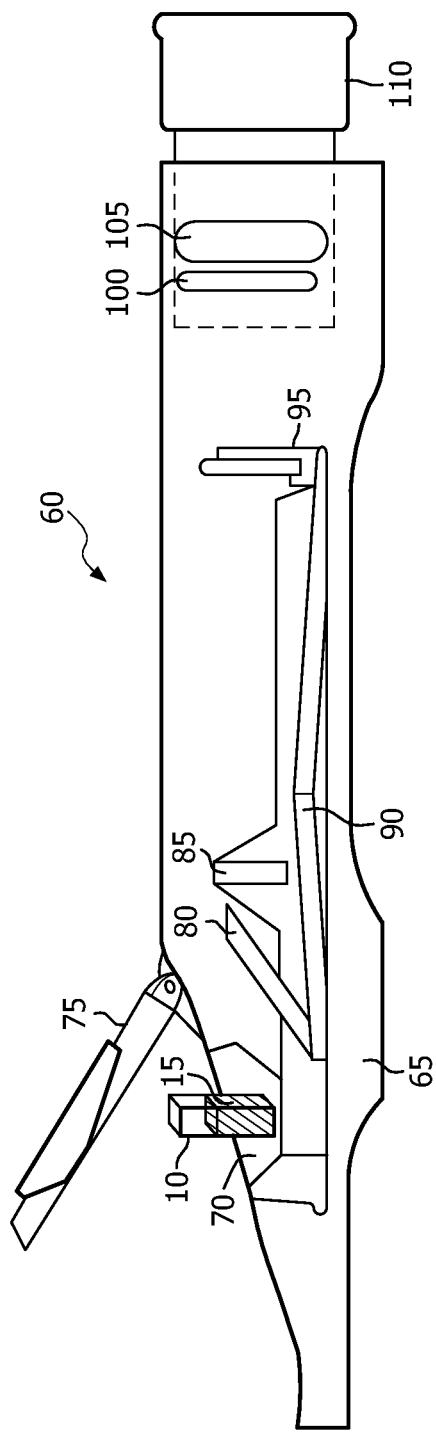
FIG. 4 is a schematic diagram of a bilirubin measuring apparatus comprising a custom, manual refractometer according to an exemplary embodiment of the present invention.
Figure 5:
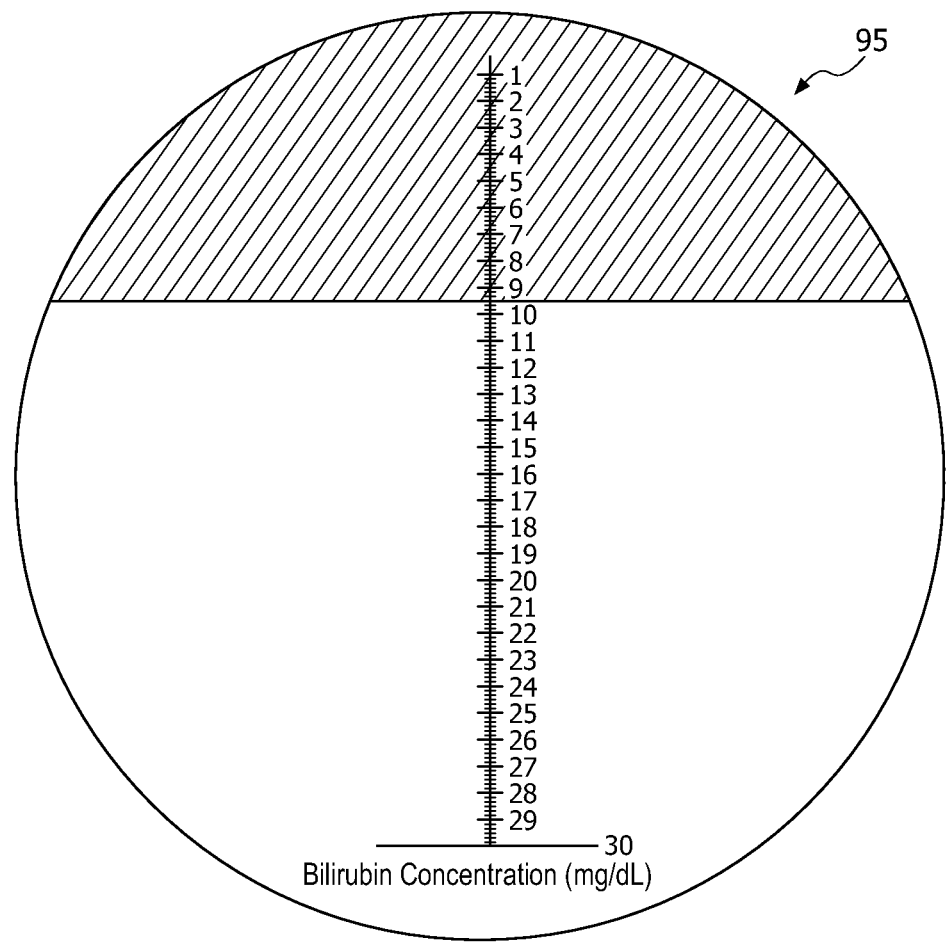
FIG. 5 is a schematic diagram of an exemplary reticle forming part of the bilirubin measuring apparatus of FIG. 4.

FIG. 4 is a schematic diagram of bilirubin measuring apparatus 60 comprising a custom, manual refractometer according to an exemplary embodiment of the present invention. Bilirubin measuring apparatus 60 includes housing 65, which in the exemplary embodiment is an impact resistant housing. The front portion of bilirubin measuring apparatus 60 includes measurement surface 70 that includes a prism and illuminating mechanism 75 that includes a light source, such as a battery powered LED, structured to emit light along the longitudinal axis of housing 65. In the exemplary embodiment, measurement surface 70 includes provision, such as a recess, for receiving and holding sample holder 10 containing liquid sample 15. The mid-portion of bilirubin measuring apparatus 60 further includes optical wedge 80, lens 85, bi-metal strip 90 and reticle 95. Bi-metal strip is structured to move optical wedge 80 and lens 85 in response to temperature changes, ensuring that readings are accurate regardless of temperature. Reticle 95 is a custom reticle/scale that directly depicts bilirubin concentration as described above. An exemplary reticle 95 is shown in FIG. 5. Finally, the rear portion of bilirubin measuring apparatus 60 includes lenses 100 and 105 and eyepiece 110.

In operation, sample holder 10 containing liquid sample 15 of interest is placed on measuring surface 70 beneath illuminating mechanism 75. The user then looks through eyepiece 110 and presses the illuminating mechanism 75 down, causing it to emit light along the longitudinal axis of housing 65. As the emitted light passes through sample holder 10 containing liquid sample 15 it slows (compared to the speed it travels in air) and is bent. Optical wedge 80 and lens 85 focus this bent light on reticle 95. Reticle 95 is magnified by lenses 100 and 105 so it is easily visible through eyepiece 110 (see FIG. 5). The user is than able to take a reading of the bilirubin concentration of sample 15 at the point where the contrast line (difference between light and dark areas) crosses the scale of reticle 95 (in FIG. 5, the reading would be approximately 9.5 mg/dL).

In an alternative embodiment, the components of apparatus 5 may be included within a housing (similar to housing 65 shown in FIG. 4) to provide a handheld, digital bilirubin measuring apparatus that may be used to estimate bilirubin concentration levels in the near patient environment. In the exemplary embodiment, such a bilirubin measuring apparatus would have a small form factor and would be able to make accurate estimates of bilirubin concentration levels using relatively small sample volumes. In particular, as noted above, each photodiode in photodiode array 40 would have a particular angle $\theta_2$ and adjusted $\theta_2$ associated with it. Thus, for each such photodiode and associated adjusted $\theta_2$, Snell's law can be used to determine a refractive index R of bilirubin, and the equation $C(mg/dL)=R/\epsilon l$ can then be used (with the calibration information) to obtain a bilirubin concentration level C for each refractive index R. Accordingly, in the end, each photodiode in photodiode array 40 would have a particular bilirubin concentration level C associated with it. As noted above, controller 45 includes a processing portion and a memory portion. In this particular embodiment, controller 45 would be programmed to store the particular bilirubin concentration level C associated with each photodiode in photodiode array 40. Controller 45 would also be programmed to cause light source 20 to emit light toward a sample holding portion (e.g. a recess) of the housing when a serum sample of interest (i.e., from a patient of interest) is placed in sample holder 10 and sample holder is placed in the sample holding portion (or when a disposable sample holder 10 having the serum sample of interest therein is inserted into the sample holding portion in the housing), to determine the particular photodiode in photodiode array 40 that registers the peak intensity, and to output via display 50 the particular bilirubin concentration level C associated with that photodiode.

The components of apparatus 5 may be also included within a housing to provide a handheld, digital bilirubin measuring apparatus that may be used to estimate bilirubin concentration levels in the near patient environment according to still a further alternative embodiment. In this further alternative embodiment, during the calibration phase, a number of different serum samples each having a different known bilirubin concentration are provided as liquid sample 15, and the associated angle $\theta_2$ is determined for each. This is similar to the calibration phase described above in connection with the first embodiment. However, in this embodiment, using ordinary least square fitting, a regression equation can be derived using that data which relates angle $\theta_2$ to bilirubin concentration in the sample holder 10 (the regression equation allows one to predict bilirubin concentration from measured angle $\theta_2$). In this embodiment, controller 45 would be programmed to include that regression equation. Controller 45 would also be programmed to cause light source 20 to emit light when a serum sample of interest (i.e., from a patient of interest) is placed in sample holder 10 (or when a disposable sample holder 10 having the serum sample of interest therein is inserted into the housing), to determine the particular photodiode in photodiode array 40 that registers the peak intensity, to determine the angle $\theta_2$ associated with that photodiode, to use the regression equation to get bilirubin concentration from that angle $\theta_2$, and to output via display 50 the determined bilirubin concentration level.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A bilirubin measuring apparatus comprising: a sample holding portion for holding at least a sample to be analyzed; a light source for directing light toward the sample holding portion; and a bilirubin measurement unit configured to determine a concentration of bilirubin in the sample based on an amount which the light is refracted while passing through the sample holding portion when at least the sample is held at the sample holding portion, wherein the bilirubin measurement unit includes a photo detector array having a plurality of photo detectors, and a controller coupled to the photo detector array, the controller being configured to (i) identify at least one of the elements of the photodetector that detects a peak intensity in response to the light after it has been refracted while passing through the sample holding portion, and (ii) determine the concentration of bilirubin in the sample based on the identified one or more of the photo detectors.

2. The bilirubin measuring apparatus according to claim 1, wherein the sample holding portion is structured to hold a sample holder in which the sample is provided, wherein the bilirubin measurement unit determines the concentration of bilirubin in the sample based on the amount which the light is refracted while passing through the sample holding portion when at least the sample holder including the sample is held at the sample holding portion.

3. The bilirubin measuring apparatus according to claim 1, wherein the sample holder is a non-disposable cuvette, a disposable cuvette, or a disposable micro-fluidic cartridge.

4. The bilirubin measuring apparatus according to claim 1, wherein the bilirubin measurement unit includes a reticle having a plurality of bilirubin concentration levels provided thereon, and wherein the concentration of bilirubin in the sample is indicted by a contrast line provided on the reticle in response to the light after it has been refracted while passing through the sample holding portion.

5. The bilirubin measuring apparatus according to claim 4, wherein the bilirubin measurement unit includes one or more optical components for focusing the light after it has been refracted while passing through the sample holding portion on the reticle.

6. The bilirubin measuring apparatus according to claim 4, wherein each of the bilirubin concentration levels is provided at a respective a position on the reticle, wherein each of the positions on the reticle also corresponds to an index of refraction, wherein the bilirubin concentration level at each position is determined based on the index of refraction corresponding to the position and calibration information obtained during a calibration phase, the calibration information being obtained during the calibration phase using a plurality of calibration samples each having a known bilirubin concentration.

7. The bilirubin measuring apparatus according to claim 1, wherein each of photo detectors has a bilirubin concentration level associated with it, and wherein the controller is adapted to determine that the concentration of bilirubin in the sample is equal to the bilirubin concentration level associated with the identified one or more of the photo detectors.

8. The bilirubin measuring apparatus according to claim 7, wherein each of the photo detectors has an angle of refraction associated with it based on a position of the photo detector array relative to the sample holding portion, and wherein for each of the photo detectors, the bilirubin concentration level associated therewith is determined during a calibration phase based on the angle of refraction associated with the photo detector.

9. A method of measuring bilirubin in a sample, comprising: holding at least the sample at a sample holding position; directing light toward the sample holding position so that the light will pass through the sample; and determining a concentration of bilirubin in the sample based on an amount which the light is refracted while passing through the sample holding position, further comprising providing a photo detector array having a plurality of photo detectors, wherein the determining comprises identifying at least one of the photodetectors that detects a peak intensity responsive to the light after it has been refracted while passing through the sample holding position, and determining the concentration of bilirubin in the sample based the identified one or more of the photo detectors.

10. The method according to claim 9, wherein the holding comprises holding a sample in which the sample is provided, wherein the determining comprises determining the concentration of bilirubin in the sample based on the amount which the light is refracted while passing through the sample holder and the sample.

11. The method according to claim 9, further comprising providing a reticle having a plurality of bilirubin concentration levels provided thereon, wherein the determining comprises indicating the concentration of bilirubin in the sample by providing a contrast line on the reticle responsive to the light after it has been refracted while passing through the sample holding position.

12. The method according to claim 11, wherein each of the bilirubin concentration levels is provided at a respective a position on the reticle, wherein each of the positions on the reticle also corresponds to an index of refraction, wherein the method further comprises determining the bilirubin concentration level at each position based on: (i) the index of refraction corresponding to the position, and (ii) calibration information obtained using a plurality of calibration samples each having a known bilirubin concentration.

13. The method according to claim 9, wherein each of photo detectors has a bilirubin concentration level associated with it, and wherein the concentration of bilirubin in the sample is determined to be equal to the bilirubin concentration level associated with the identified one or more of the photo detectors.

14. The method according to claim 13 wherein each of photo detectors has an angle of refraction associated with it based on a position of the photo detector array relative to the sample holding position, and wherein the method further comprises determining, for each of the photo detectors, the bilirubin concentration level associated therewith during a calibration phase based on the angle of refraction associated with the photo detector.

15. A method of measuring bilirubin including a sample holding portion for holding at least a sample to be analyzed, a light source for directing light toward the sample holding portion, and a bilirubin measurement unit configured to determine a concentration of bilirubin in the sample based on an amount which the light is refracted while passing through the sample holding portion when at least the sample is held at the sample holding portion, the method comprising: using a plurality calibration samples each having a known concentration of bilirubin to determine an equation relating refractive index of bilirubin to bilirubin concentration; and using the equation to determine the concentration of bilirubin in the sample, wherein the bilirubin measurement unit includes a photo detector array having a plurality of photo detectors, and a controller coupled to the photo detector array, the controller being configured to (i) identify one or more of the photo detectors that detects a peak intensity in response to the light after it has been refracted while passing through the sample holding portion, and (ii) determine the concentration of bilirubin in the sample based on the identified one or more of the photo detectors, wherein each of photo detectors has a bilirubin concentration level associated with it, and wherein the controller is configured to determine that the concentration of bilirubin in the sample is equal to the bilirubin concentration level associated with the identified one or more of the photo detectors, wherein each of photo detectors has an angle of refraction associated with it based on a position of the photo detector array relative to the sample holding portion, and wherein the equation is use make a concentration measurement comprising determining for each of the photo detectors the bilirubin concentration level associated therewith using the angle of refraction associated with the photo detector and the equation.

16. The method according to claim 15, wherein the bilirubin measurement unit includes a reticle having a plurality of bilirubin concentration levels provided thereon, wherein the concentration of bilirubin in the sample is indicted by a contrast line provided on the reticle in response to the light after it has been refracted while passing through the sample holding portion, wherein each of the bilirubin concentration levels is provided at a respective a position on the reticle, wherein each of the positions on the reticle also corresponds to an index of refraction, and wherein the equation is used to make a concentration measurement comprising determining the bilirubin concentration level at each position using the index of refraction corresponding to the position and the equation.

17. The method according to claim 15, wherein the using the plurality calibration samples comprises: (i) for each of the calibration samples directing calibration light toward at least the calibration sample at a first angle and measuring a second angle of the calibration light after being refracted by at least the calibration sample, and (ii) determining the equation using the known concentration of bilirubin and the second angle associated with each calibration sample using regression.

* * * * *